United States Patent
Bosworth

(10) Patent No.: US 11,911,019 B2
(45) Date of Patent: Feb. 27, 2024

(54) ALL-SUTURE ANCHOR

(71) Applicant: Conmed Corporation, Utica, NY (US)

(72) Inventor: Adrian Bosworth, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 76 days.

(21) Appl. No.: 16/033,616

(22) Filed: Jul. 12, 2018

(65) Prior Publication Data

US 2019/0015092 A1 Jan. 17, 2019

Related U.S. Application Data

(60) Provisional application No. 62/532,119, filed on Jul. 13, 2017.

(51) Int. Cl.
*A61B 17/04* (2006.01)
*A61B 17/17* (2006.01)

(52) U.S. Cl.
CPC .......... *A61B 17/0401* (2013.01); *A61B 17/17* (2013.01); *A61B 2017/042* (2013.01); *A61B 2017/0403* (2013.01); *A61B 2017/0404* (2013.01); *A61B 2017/0445* (2013.01); *A61B 2017/0464* (2013.01)

(58) Field of Classification Search
CPC ........ A61B 17/0401; A61B 2017/0403; A61B 2017/0404; A61B 2017/0406; A61B 2017/0414; A61B 2017/042; A61B 2017/0422; A61B 2017/0445; A61F 2/0045
See application file for complete search history.

(56) References Cited

U.S. PATENT DOCUMENTS

| | | |
|---|---|---|
| 4,549,545 A | 10/1985 | Levy |
| 4,741,330 A | 5/1988 | Hayhurst |
| 5,403,348 A | 4/1995 | Bonutti |
| 5,423,860 A | 6/1995 | Lizardi et al. |
| 5,540,703 A | 7/1996 | Barker, Jr. et al. |

(Continued)

FOREIGN PATENT DOCUMENTS

| | | |
|---|---|---|
| EP | 0611551 | 8/1994 |
| WO | WO1999/039644 | 8/1999 |

(Continued)

OTHER PUBLICATIONS

European Patent Office Report, EPO Form 2001, Application No. 12 748 076.2, pp. 1-4, dated Mar. 2, 2017.

(Continued)

*Primary Examiner* — Thomas McEvoy
(74) *Attorney, Agent, or Firm* — Bond, Schoeneck & King, PLLC; Frederick J. M. Price

(57) ABSTRACT

An anchor includes a flat fibrous construct having an open elongated column; and a filament having a first filament end and a second filament end, which passes through and is positioned at least partially in the open elongated column. The flat fibrous construct includes a first state in which the flat fibrous construct is uncompressed and extends along the longitudinal axis of the filament when in an unfolded and pre-deployed condition; and a second state in which the flat fibrous construct is compressed and expanded in a direction perpendicular to longitudinal axis of the filament in a deployed condition.

11 Claims, 4 Drawing Sheets

(56) References Cited

U.S. PATENT DOCUMENTS

| | | |
|---|---|---|
| 5,584,695 A | 12/1996 | Lal Sachdeva et al. |
| 5,989,252 A | 11/1999 | Fumex |
| 6,511,498 B1 | 1/2003 | Fumex |
| 6,544,281 B2 | 4/2003 | Elattrache et al. |
| 6,991,636 B2 | 1/2006 | Rose |
| 7,066,956 B2 | 6/2006 | Wayne |
| 7,077,863 B2 | 7/2006 | Schmieding et al. |
| 7,118,581 B2 | 10/2006 | Friden |
| 7,306,626 B2 | 12/2007 | Whelan |
| 7,390,329 B2 | 6/2008 | Westra et al. |
| 7,556,640 B2 | 7/2009 | Foerster |
| 7,588,595 B2 | 9/2009 | Miller et al. |
| 7,749,250 B2 | 7/2010 | Stone et al. |
| 7,972,292 B2 | 7/2011 | Behl et al. |
| 7,988,697 B2 | 8/2011 | Miller et al. |
| 8,128,698 B2 | 3/2012 | Bentley et al. |
| 8,298,262 B2 | 10/2012 | Stone et al. |
| 8,303,604 B2 | 11/2012 | Stone et al. |
| 8,361,113 B2 | 1/2013 | Stone et al. |
| 8,409,225 B2 | 4/2013 | Bull et al. |
| 8,425,554 B2 | 4/2013 | Denove et al. |
| 8,449,552 B2 | 5/2013 | Sanders |
| 8,500,809 B2 | 8/2013 | Saliman et al. |
| 8,506,597 B2 | 8/2013 | Kaiser et al. |
| 8,562,647 B2 | 10/2013 | Kaiser et al. |
| 8,579,553 B2 | 11/2013 | Pierce |
| 8,621,961 B2 | 1/2014 | Burch et al. |
| 8,652,172 B2 | 2/2014 | Denham et al. |
| 8,734,491 B2 | 5/2014 | Seavey |
| 8,795,334 B2 | 8/2014 | Astorino et al. |
| 8,828,053 B2 | 9/2014 | Sengun et al. |
| 8,876,900 B2 | 11/2014 | Guederian et al. |
| 8,888,795 B2 | 11/2014 | Chu |
| 8,888,848 B2 | 11/2014 | Saliman et al. |
| 8,951,285 B2 | 2/2015 | Sugimoto et al. |
| 9,078,651 B2 | 7/2015 | Astorino et al. |
| 9,138,223 B2 | 9/2015 | Jolly et al. |
| 9,173,645 B2 | 11/2015 | Overes et al. |
| 9,204,874 B2 | 12/2015 | Denove et al. |
| 9,370,352 B2 | 6/2016 | Astorino et al. |
| 9,445,804 B2 | 9/2016 | Paulos |
| 9,538,998 B2 | 1/2017 | Stone et al. |
| 9,549,730 B2 | 1/2017 | Oba et al. |
| 9,603,591 B2 | 3/2017 | Denham et al. |
| 9,788,826 B2 | 10/2017 | McCartney |
| 9,795,398 B2 | 10/2017 | Steiner et al. |
| 9,800,027 B1 | 10/2017 | Pierce |
| 9,801,719 B2 | 10/2017 | Miraki |
| 9,826,971 B2 | 11/2017 | Lombardo et al. |
| 9,848,868 B2 | 12/2017 | Saliman |
| 9,913,638 B2 | 3/2018 | Saliman et al. |
| 9,918,711 B2 | 3/2018 | Seavey |
| 10,136,886 B2 | 11/2018 | Norton et al. |
| 10,143,469 B2 | 12/2018 | Denove et al. |
| 10,631,844 B2 | 4/2020 | Astorino et al. |
| 2004/0243135 A1 | 12/2004 | Koseki |
| 2006/0074422 A1 | 4/2006 | Story et al. |
| 2007/0156174 A1 | 7/2007 | Kaiser et al. |
| 2007/0185532 A1* | 8/2007 | Stone ................. A61B 17/0482 606/232 |
| 2007/0276395 A1 | 11/2007 | Burn |
| 2009/0062850 A1 | 3/2009 | Ken |
| 2009/0076547 A1 | 3/2009 | Sugimoto et al. |
| 2009/0171360 A1 | 7/2009 | Whelan |
| 2011/0087248 A1 | 4/2011 | Steffen |
| 2011/0238071 A1 | 9/2011 | Fernandez-Scoma |
| 2012/0003057 A1 | 1/2012 | Leyba |
| 2012/0071878 A1 | 3/2012 | Cowin |
| 2012/0197395 A1 | 8/2012 | Berg |
| 2012/0197396 A1 | 8/2012 | Berg |
| 2012/0290004 A1* | 11/2012 | Lombardo ......... A61B 17/0401 606/232 |
| 2013/0218273 A1 | 8/2013 | Bull et al. |
| 2014/0052178 A1* | 2/2014 | Dooney, Jr. ........ A61B 17/0401 606/232 |
| 2014/0277133 A1* | 9/2014 | Foerster ............. A61B 17/0401 606/232 |
| 2014/0330307 A1 | 11/2014 | Steffen |
| 2015/0133941 A1 | 5/2015 | Saylor et al. |
| 2016/0287242 A1* | 10/2016 | Troxel ................. A61L 31/045 |
| 2017/0143551 A1* | 5/2017 | Coleman ........... A61B 17/0482 |
| 2018/0049755 A1 | 2/2018 | Laviano et al. |

FOREIGN PATENT DOCUMENTS

| | | |
|---|---|---|
| WO | WO2007/005394 | 1/2007 |
| WO | WO2009/029914 | 3/2009 |

OTHER PUBLICATIONS

Ronald Glousman, M.D. and Nicholas Sgaglione, M.D., Labral Repair, JuggerKnot Soft Anchor brochure, 2010, 2011, 12 pages.

* cited by examiner

ALL-SUTURE ANCHOR

CROSS-REFERENCE TO RELATED APPLICATION

The present application claims priority to and the benefit of U.S. Provisional Patent Application No. 62/532,119 filed on Jul. 13, 2017, which is incorporated by referenced in its entirety herein.

BACKGROUND OF THE INVENTION

1. Field of the Invention

The present invention relates to an all-suture anchor construct for fixation in a bone hole or tunnel and, more particularly, to an all-suture anchor construct having a flat section of woven suture tape, braid or fibrous construct including an open column of suture tape/fibrous construct material woven therein with a length of a suture or filament positioned through the open column.

2. Description of Related Art

Many orthopedic surgical and medical procedures require the fixation of one body to another body. Such bodies may include bone, soft tissue, and prosthetics. One body can be fixed in a position relative to another using connector devices, such as screws and suture anchors (e.g., cannulated knotless suture anchors and soft all-suture anchors). For example, various orthopedic surgeries require the insertion and fixation of a suture anchor within a bone hole. Suture anchors can include "hard" suture anchors, and "soft" all-suture anchors.

As described in U.S. Pat. No. 8,409,252, for example, "non-soft," "hard" or "rigid" suture anchors generally include a "hard" anchor body portion (that may or may not include inner and outer members) and a suture/filament portion. The anchor body of such suture anchors may be formed of a biocompatible and/or bioabsorbable material. These materials may be of such composition that they are reabsorbed by the body, e.g., during the healing process of the bone. Exemplary materials that are suitable for use in the inner and outer members include, but are not limited to, polyetheretherketone ("PEEK"), polylactic acid/beta-trical-cium phosphate ("PLA/Beta-TCP") composites, ultra-high molecular weight polyethylene ("UHMWPE"), as well as other metallic, non-metallic, and polymeric materials.

Since soft anchors are commonly made entirely of suture materials, they are sometimes called "all-suture" anchors, and generally include a fibrous construct anchor body portion (or fibrous, braided or woven fabric-type structure such as a flexible web, as described in U.S. Pat. No. 9,173,652) and a suture or filament portion. Another example of a "soft" all-suture anchor is the Y-Knot® device. See, e.g., U.S. Pat. No. 9,826,971. Such soft all-suture anchors are often preferred by some orthopedic surgeons over the hard suture anchors, the reasons of which should be understood by a person of ordinary skill in the art. In a traditional Y-Knot device, a suture filament is pierced entirely through a braid material a number of times, such that the suture passes through a "front" surface and a "back" surface.

There are at least two general, conventional methods for inserting a suture anchor within a bone. In one method, a bone hole is created and prepared using a drill bit. The drill bit is typically advanced through a drill guide to create the bone hole and then, a suture anchor is passed through or down the drill guide with an anchor inserter/installation device into the bone hole for deployment.

In a second method, the drilling step is eliminated in an attempt to avoid the aforementioned misalignment issue. A self-punching suture anchor, such as the Y-Knot® RC suture anchor, for example, is designed with an inserter that allows the anchor in the inserter to be directly positioned on the bone at the desired location. When the anchor in the inserter is positioned at the desired location, the inserter can be hammered, forcing the anchor directly into the bone.

Conventional methods and devices for inserting/deploying such all-suture anchors are known, examples of which are disclosed in U.S. Pat. No. 9,173,652.

When certain conventional all-suture anchors are constructed in the traditional manner, segments of suture filament on the back surface of the braid are in contact with bone and may be abraded by the bone due to friction upon deployment and post-deployment of the device.

Therefore, there is a need for a soft all-suture anchor construct that can protect the suture filament from being abraded by bone due to friction upon deployment and post-deployment of the construct.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention recognize that there are potential problems and/or disadvantages with conventional soft all-suture anchors (as discussed herein and above). Various embodiments of the present invention may be advantageous in that they may solve or reduce one or more of the potential problems and/or disadvantages discussed herein.

The present disclosure is directed to an inventive configuration, structure, and resulting function of a soft all-suture anchor. In one embodiment, an all-suture anchor is disclosed and can include, but is not limited to, a flat fibrous construct having a first end and a second end, and an open elongated column/lumen extending from a first end to a second end; and a filament having a first end and a second end passing through and positioned at least partially in the open column. In an embodiment, the filament is free to slide through the open column such that the filament can be removed from the open column from the first end of the fibrous construct and the second end of the fibrous construct. An embodiment of the flat fibrous construct can also be tubular in addition to having an open elongated column/lumen. The flat tape/fibrous construct may either be woven in situ directly onto the filament (e.g., a round section suture braid), or woven with an open column into which the round section suture braid may be later inserted. Embodiments of the all-suture anchor described herein, are formed, in part from a fibrous construct which is retained within preformed bone holes by being deformable upon deployment to increase its diameter/thickness to a size greater than that of the bone hole, and to thereby reside within cancellous bone and under the bone cortex.

According to another embodiment, the all-suture anchor briefly described above in conjunction with an installation device is provided. The installation device can include, but is not limited to, a handle and a distal deployment end, which can be fork-shaped or other appropriate shape to sufficiently hold during deployment and to deploy the all-suture anchor within a bone hole.

According to yet another embodiment, a method of deploying the all-suture anchor briefly described above in a preformed bone hole (already drilled) can include, but is not limited to, the steps of: (i) providing the all-suture anchor briefly described above; and (ii) using the installation device to deploy the all-suture anchor into the preformed bone hole (preferably into cancellous bine below the cortex) by tensioning the free ends of the filament (applying a force on the free ends of the filament in a direction away from the bone hole). In brief, the tensile force applied to the suture tails causes the flat tape/fibrous construct to "form a clump" and "ball-up" underneath the cortical layer and thus provide fixation for the anchor Suture material, sutures, or filaments as the terms are used and described herein, can include monofilament or multi-filament suture as well as any other metallic or non-metallic filamentary or wire-like material suitable for performing the function of a suture. This material can include both bioabsorbable and non-absorbable materials, and can be round, flat, or braided.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Figure 1:
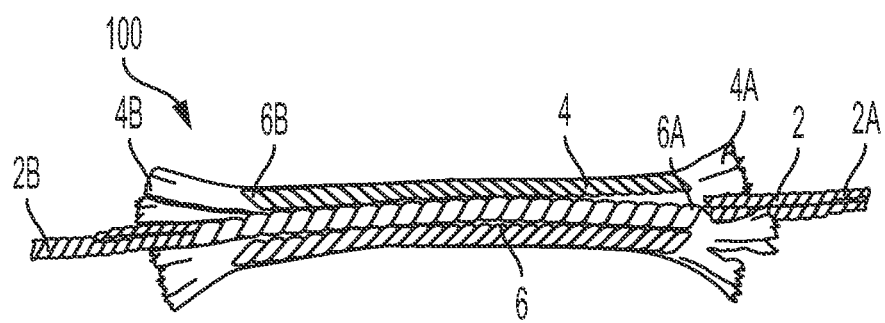
FIG. 1 is a perspective view schematic representation of a soft all-suture anchor in an unloaded (not loaded onto an installation device), pre-deployment configuration according to an embodiment.

Referring now to the drawings, wherein like reference numerals refer to like parts throughout, there is seen in FIG. 1 a perspective view schematic representation of a soft all-suture anchor 100 in an unloaded (not loaded onto an installation device), pre-deployment configuration, according to an embodiment. The all-suture anchor 100 can include, but is not limited to, a flat fibrous construct 4 having a first end 4A, a second end 4B, and an open elongated column/lumen 6 having a first end 6A and the second end 6B (each of the first end 6A and the second end 6B of the open elongated column/lumen 6 can extend between or beyond the first 4A and second 4B ends of the flat fibrous construct). The open elongated column/lumen 6 can be woven along an axis that is parallel to or along a central axis of the flat fibrous construct 4, or can be woven along a path that is not parallel to the central axis. As shown in FIG. 1, the open elongated column/lumen is woven along the central axis.

Still referring to FIG. 1, a filament 2 is shown having a first end 2A and a second end 2B, and passing through and at least partially positioned in the open column 6. In an embodiment, the filament 2 is free to slide through the open column 6 such that the filament 2 can be removed from the open column 6 from the first end 2A of the fibrous construct 2 and/or the second end 2B of the fibrous construct 2. In accordance with an alternative embodiment, the filament is locked and not slidable through the open column 6.

Figure 2A:
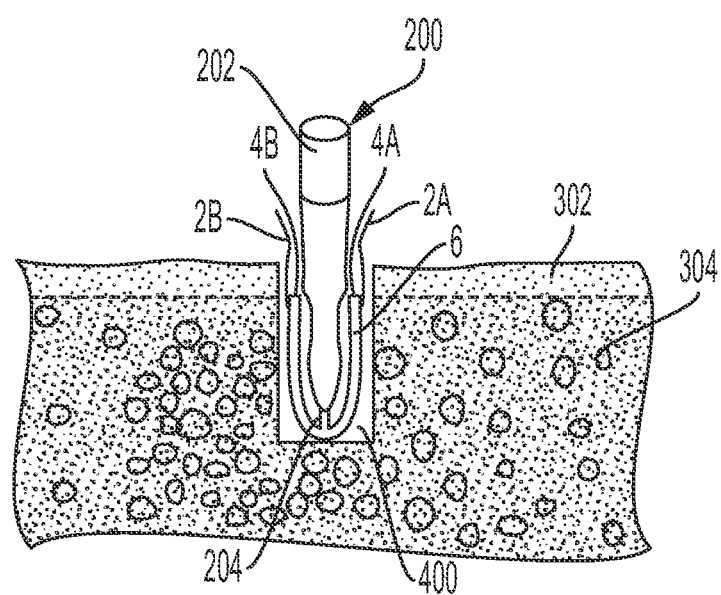
FIG. 2A is a side view schematic representation of an embodiment of the all-suture anchor of FIG. 1 connected to an installation device in a pre-deployment configuration according to an embodiment.
Figure 2B:
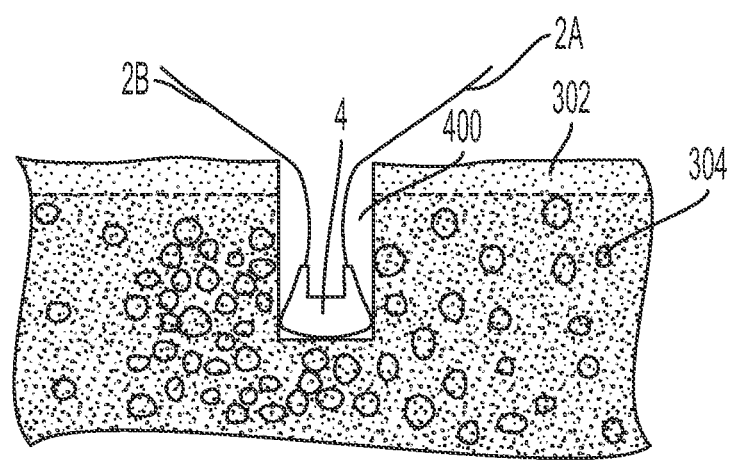
FIG. 2B is a side view schematic representation of an embodiment of the all-suture anchor of FIG. 1 in a post-deployment configuration positioned in a bone hole according to an embodiment.
Figure 2C:
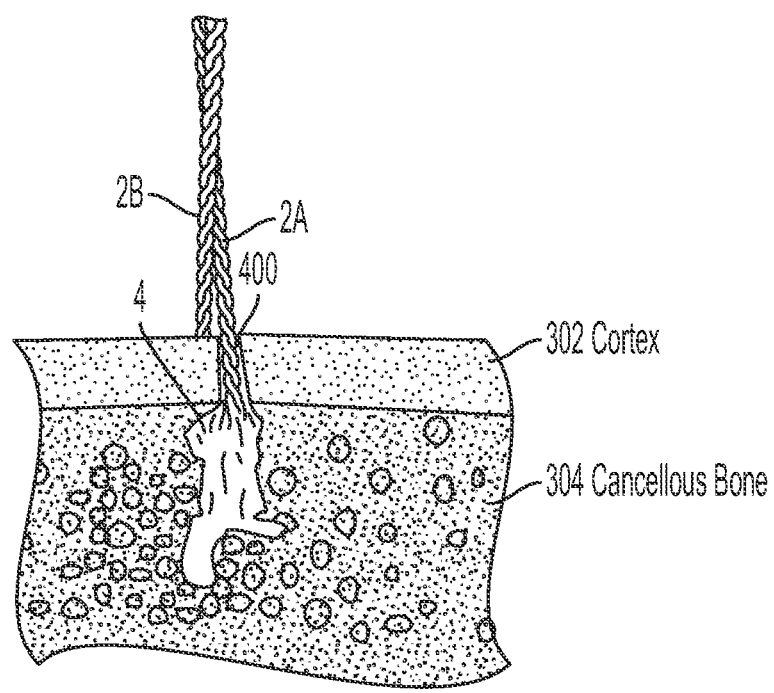
FIG. 2C a side view digital photograph of an embodiment of the all-suture anchor of FIG. 1 in a post-deployment configuration positioned in a bone hole according to an embodiment.

Turning now to FIGS. 2A and 2B, there are shown side view schematic representations of an embodiment of the all-suture anchor 100 in the pre-deployment and post-deployment configurations. As described above, the all-suture anchor 100 contains at least two sections: at least one suture 2 with a first end 2A and a second end 2B; and an anchor body/fibrous construct 4 with a first end 4A and a second end 4B, and an open elongated column/lumen 6 extending from a first end 6A to a second end 6B, which is to form a portion of the anchor 100 that can increase in width, thickness and/or diameter and shrink in length as part of deployment.

As shown in FIG. 2A, the installation device in the pre-deployment configuration is provided. The all-suture anchor 100 is shown connected to the distal deployment end 204 of an installation device 200, which also includes a handle 202. The distal deployment end 204 and the all-suture anchor 100 are shown positioned in a bone hole 400 in cancellous bone 304 under the bone cortex 302. In order to deploy the all-suture anchor 100 (which can be connected to other tissue that needs to be brought into apposition to the bone, as should be understood by a person of ordinary skill in the art in conjunction with a review of this disclosure), the first end 2A and/or the second end 2B are pulled/tensioned in a direction away from the bone hole 400. The first end 2A and the second end 2B can be pulled/tensioned in a direction away from the bone hole 400 with or without the installation device 200 in place in the bone hole 400 (if installation device 200 is in place in the bone hole 400, it can act as a counter force to the tension force out of the hole 400 to assist with the deployment of the all-suture anchor 100).

As shown in FIG. 2B, the anchor body/fibrous construct 4 is shown "shortened" and "expanded" in the post-deployment configuration and locked in the bone hole 400, which can be additive to the increase due to pleats formed by the fibrous construct 4 (which may also be part of the fibrous construct 4). The all-suture anchor 100, and, in particular, the fibrous construct 4 takes advantage of Poisson's ratio, which captures the following cause/effect relationship: compressing a material in a first direction causes the material to expand in direction perpendicular to the first direction (i.e., if compressed in the x-direction, the material will expand in the y-direction and/or z-direction), and stretching/lengthening a material in a first direction causes the material to contract in directions perpendicular to the first direction. Although, it is the anchor body/fibrous construct 4 that increases in width, thickness and/or diameter at deployment, it should be understood that the suture 2 can also play a role in the deployment of the anchor 100 even though the suture 2 may remain free to slide in some embodiments, and non-slidable in others (at least at a particular position or point in use) in relation to the anchor body 4. The suture 2 helps to position, align and support the anchor body 4 (as should be understood by a person of skill in the art in conjunction with a review of this disclosure).

In other words, the anchor body/fibrous construct 4 has two primary functions. First, it becomes a base for the suture 2 to slide within (within the column/lumen 6). Second, when compressed and/or pleated during deployment, the anchor body 4 becomes more compact in one direction thereby expanding outwardly and increasing its overall width, thickness or diameter to create a retention capacity. This action of having the anchor body 4 change in shape to increase its overall width, thickness or diameter is a useful characteristic which may be used advantageously to secure the anchor 100 in a hole 400 or against a bony or soft tissue. It is this combination of the expanding anchor body 4 coupled with the suture 2 remaining slidable (in some embodiments; and non-slidable in others, at least at a particular position or point in use) in relation to the anchor body 204 that render embodiments of the present invention ideal for the reattachment of soft tissue to bone or soft tissue to soft tissue where it is desirable to pass sliding knots to secure a repair.

While embodiments of the present invention has been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. An anchor for placement in or against tissue, the anchor comprising:
    a non-tubular flat fibrous construct having a first fibrous construct end and a second fibrous construct end, and an open elongated column formed of fibrous construct material separately woven from the non-tubular flat fibrous construct, woven with a different pattern than the non-tubular flat fibrous construct, and extending along an axis that is parallel to or along a central axis of the non-tubular flat fibrous construct from a first elongated column end to a second elongated column end, wherein a portion of the non-tubular flat fibrous construct is adjacent to and extends from a first side and another portion of the non-tubular flat fibrous construct is adjacent to and extends from a second side of the open elongated column; and
    a filament having a first filament end and a second filament end, and passing through and positioned at least partially in the open elongated column;
    wherein the non-tubular flat fibrous construct comprises:
        a first state in which the non-tubular flat fibrous construct is uncompressed and extends along a longitudinal axis of the filament when in an unfolded and pre-deployed condition; and
        a second state in which the non-tubular flat fibrous construct is compressed and expanded in a direction perpendicular to the longitudinal axis of the filament in a deployed condition.

2. The anchor of claim 1, wherein the filament is free to slide through the open column such that the filament can be removed from the open column from the first fibrous construct end and the second fibrous construct end.

3. The anchor of claim 1, wherein at least the first filament end and the second filament end extend outside of and beyond a respective elongated column end.

4. The anchor of claim 1, wherein the fibrous construct material of the open elongated column is woven around an axis that is parallel to or along a central axis of the flat fibrous construct.

5. The anchor of claim 1, wherein a thickness of the non-tubular flat fibrous construct is greater in the deployed state as compared to the thickness of the non-tubular flat fibrous construct in an un-deployed state.

6. An anchor deployment system comprising:
    an anchor including:
        a non-tubular flat fibrous construct having a first fibrous construct end and a second fibrous construct end, and an open elongated column formed of fibrous construct material separately woven from the non-tubular flat fibrous construct, woven with a different pattern than the non-tubular flat fibrous construct, and extending along an axis that is parallel to or along a central axis of the non-tubular flat fibrous construct from a first elongated column end to a second elongated column end, wherein a portion of the non-tubular flat fibrous construct is adjacent to and extends from a first side and another portion of the non-tubular flat fibrous construct is adjacent to and extends from a second side of the open elongated column; and
        a filament having a first filament end and a second filament end, and passing through and positioned at least partially in the open elongated column;
        wherein the non-tubular flat fibrous construct comprises:
            a first state in which the flat non-tubular fibrous construct is uncompressed and extends along a longitudinal axis of the filament when in an unfolded and pre-deployed condition; and
            a second state in which the non-tubular flat fibrous construct is compressed and expanded in a direction perpendicular to a longitudinal axis of the filament in a deployed condition; and
    an installation device including distal deployment end on which the anchor is positioned and is configured to deploy the anchor into a bone hole.

7. The anchor placement system of claim 6, the distal deployment end of the installation device comprises a fork around which the anchor is positioned.

8. The anchor placement system of claim 6, wherein the filament is free to slide through the open column such that the filament can be removed from the open column from the first fibrous construct end and the second fibrous construct end.

9. The anchor placement system of claim 6, wherein at least the first filament end and the second filament end extend outside of and beyond a respective elongated column end.

10. The anchor placement system of claim 6, wherein the open elongated column is woven along an axis that is parallel to or along a central axis of the flat fibrous construct.

11. The anchor placement system of claim 6, wherein a thickness of the non-tubular flat fibrous construct is greater in the deployed state as compared to a thickness of the non-tubular flat fibrous construct in an un-deployed state.

\* \* \* \* \*